US010016760B2

(12) United States Patent
Rupley

(10) Patent No.: US 10,016,760 B2
(45) Date of Patent: Jul. 10, 2018

(54) METHOD AND APPARATUS FOR NON-COMPRESSED EVALUATION OF TISSUE SPECIMENS

(71) Applicant: Daniel Rupley, New Orleans, LA (US)

(72) Inventor: Daniel Rupley, New Orleans, LA (US)

( * ) Notice: Subject to any disclaimer, the term of this patent is extended or adjusted under 35 U.S.C. 154(b) by 232 days.

(21) Appl. No.: 15/160,908

(22) Filed: May 20, 2016

(65) Prior Publication Data
US 2017/0333892 A1 Nov. 23, 2017

(51) Int. Cl.
G01N 3/00 (2006.01)
B01L 3/00 (2006.01)
G01N 1/36 (2006.01)

(52) U.S. Cl.
CPC ........... B01L 3/505 (2013.01); G01N 1/36 (2013.01); B01L 2200/025 (2013.01); B01L 2300/042 (2013.01); B01L 2300/0832 (2013.01)

(58) Field of Classification Search
CPC ........................................................ G01N 3/00
See application file for complete search history.

(56) References Cited
U.S. PATENT DOCUMENTS

| 4,131,998 | A | 1/1979 | Spears |
| 5,383,472 | A | 1/1995 | Devlin et al. |
| 5,393,234 | A | 2/1995 | Yamada et al. |
| 5,609,827 | A | 3/1997 | Russel et al. |
| 6,238,907 | B1 | 5/2001 | Schuler-Maloney et al. |
| 6,344,026 | B1 | 2/2002 | Burbank et al. |
| 6,540,756 | B1 | 4/2003 | Vaughn |
| 2005/0112758 | A1 | 5/2005 | Archambault et al. |
| 2007/0038014 | A1 | 2/2007 | Cox et al. |
| 2008/0299605 | A1 | 12/2008 | Lary et al. |
| 2012/0058553 | A1 | 3/2012 | Haywood et al. |

Primary Examiner — Jyoti Nagpaul
(74) Attorney, Agent, or Firm — Keaty Law Firm, LLC

(57) ABSTRACT

The present invention provides a method and apparatus for evaluating the margins of a surgically-removed tissue specimen, such as a breast tissue specimen, to determine whether sufficient fatty tissue has been removed from around the lesion or cancerous point. The instant invention provides a solution to the problem of on-site evaluation of the margin sufficiency during the surgical procedure, in that it provides surgeons with an orthogonal view of all sides of the tissue specimen to be evaluated. The specimen evaluation device provides for properly-oriented examination of the removed specimen in a non-compressed, undistorted manner, both by visual inspection and through radiographic evaluation. Through this examination of the properly-oriented specimen, the surgeon may quickly and more accurately be informed of whether there remain cancerous cells in the margins surrounding the sample, which are meant to be free of cancerous cells. Upon evaluation of the margins of the removed sample, the surgeon may then make an on-site determination on whether to proceed with additional surgery or complete the surgical procedure.

20 Claims, 4 Drawing Sheets

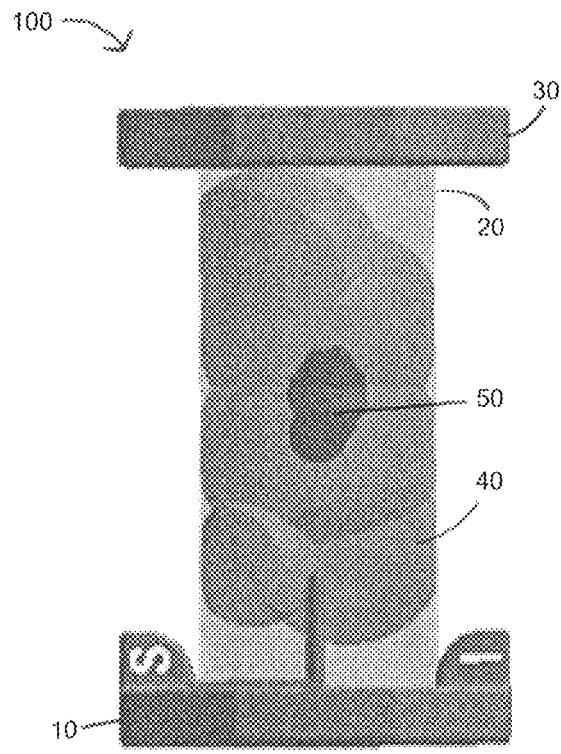
FIGURE 1
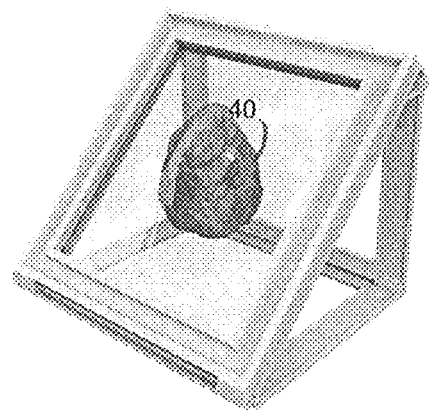
FIGURE 2 – PRIOR ART

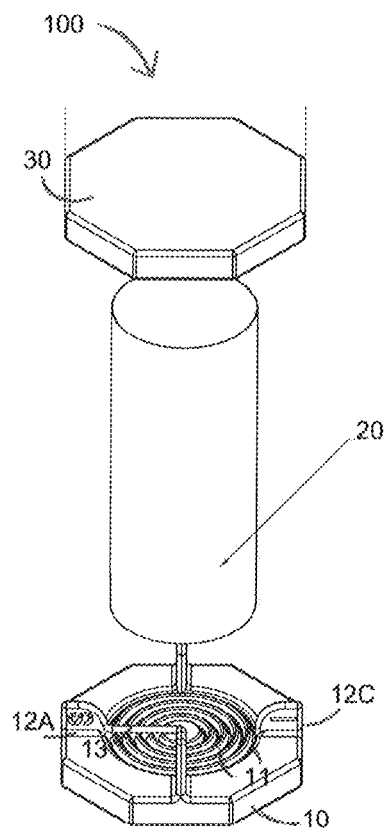
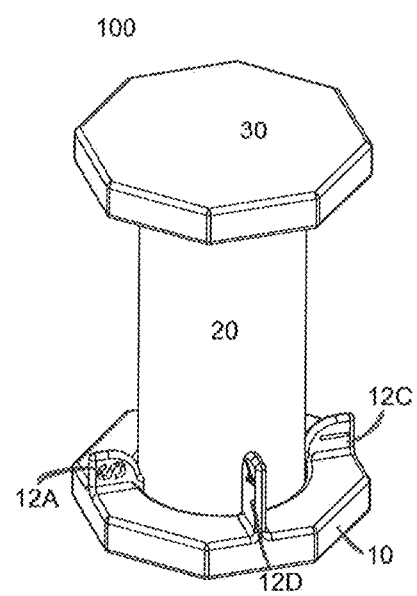
FIGURE 9
FIGURE 10
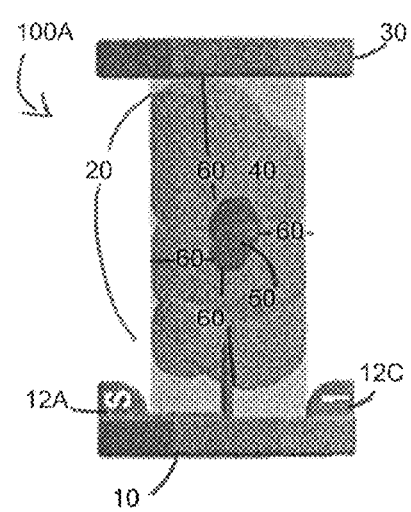
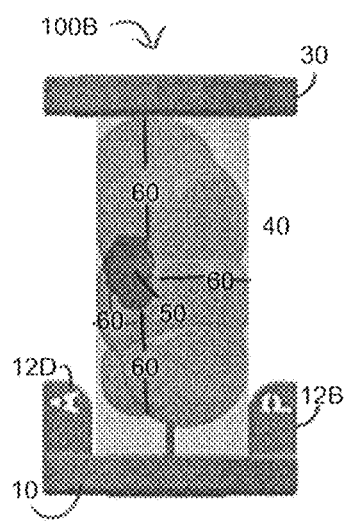
FIGURE 11

METHOD AND APPARATUS FOR NON-COMPRESSED EVALUATION OF TISSUE SPECIMENS

BACKGROUND OF THE INVENTION

The present invention provides a method and apparatus for evaluating the margins of a surgically-removed tissue specimen, such as a breast tissue specimen, to determine whether sufficient fatty tissue has been removed from around the lesion or cancerous point. The instant invention provides a solution to the problem of on-site evaluation of the margin sufficiency during the surgical procedure, in that it provides surgeons with an orthogonal view of all sides of the tissue specimen to be evaluated. The specimen evaluation device provides for properly-oriented examination of the removed specimen in a non-compressed, undistorted manner, both by visual inspection and through radiographic evaluation. Through this examination of the properly-oriented specimen, the surgeon may quickly and more accurately be informed of whether there remain cancerous cells in the margins surrounding the sample, which are meant to be free of cancerous cells. Upon evaluation of the margins of the removed sample, the surgeon may then make an on-site determination on whether to proceed with additional surgery or complete the surgical procedure.

When a patient undergoes a surgery to remove a cancerous lump, one of the challenges a surgeon faces is removal of the appropriate amount of tissue from the patient. The surgeon must ensure that sufficient tissue is removed such that the cancerous cells are removed from the body of the patient. Conversely, the surgeon will attempt to make the removal site as contained as possible so as to disturb the body of the patient as little as possible. This may be especially appropriate in the case of breast cancer removal, in which a patient may be particularly sensitive to the removal of large amounts of breast tissue. Additionally, some biopsies are undergone as preventative measures, and a surgeon will be removing tissue samples prior to confirming the presence or absence of cancerous cells. In such a scenario, the surgeon may attempt to remove only a small tissue sample.

Because a surgeon may be attempting removal of a relatively small tissue sample from a patient, evaluation of the tissue sample is required after its removal. Such evaluation may be visual inspection by a surgeon or pathologist, but is more commonly undergone via radiographic evaluation to ensure complete and thorough analysis of the tissue sample. A successful removal of cancerous tissue would include a certain "padding" of cancer-free tissue surrounding the cancerous cells to ensure that the entirety of the cancerous site was removed from the patient. The relative distance away from the edges of the removed sample is referred to as the "margins" of the sample. In a successful removal, such margins would be clear of cancerous cells. If, however, the margins of the removed tissue feature cancerous cells, then the surgeon may have to remove additional tissue from the patient to ensure the cancer was fully removed from the patient. For example, in colloquial terms, a surgeon may remove a tissue sample with a height of five millimeters and width of six millimeters. The surgeon may have previously predicted that the cancerous cells would be contained to the middle section of the removed tissue, such that two millimeters on each of the four edges of the tissue sample are expected to be free of cancerous cells. If, upon evaluation of the removed sample, there remain cancerous cells in any one of these two-millimeter margins, then the surgeon will have to remove an additional section of tissue from the patient. The margins of that sample would then also be evaluated, and once it is determined the margins are clear, then the patient may be confident that the cancerous site was fully removed from his or her body.

It may be appreciated from the above that instances often arise wherein the surgeon has not removed a sufficiently-sized tissue sample, and must conduct a second removal of tissue from the patient. Without the benefit of on-site margin evaluation, the surgeon would not be aware of the need of the second procedure until after the full completion of the first surgery. Thus, the patient would have to undergo an entire second surgical procedure to ensure the full removal of the cancerous site.

Further, in addition to evaluating such tissue margins on-site, it is desirable to provide a complete evaluation of the tissue sample. Some procedures may allow for on-site evaluation of a two-dimensional representation of the tissue sample, such as discussed above. However, a tissue sample, as three-dimensional material, features six sides and its six corresponding margins. Each of these margins must be evaluated to determine whether the margins are clear and the patient's cancer has been sufficiently removed. To fully evaluate all six sides of the sample, in an orthogonal view, the sample itself must be suspended in a non-compressed manner that allows for a fully rotational view of the tissue sample.

However, when a sample is suspended in a manner such that it may be evaluated from every angle, the relative orientation of the sample may be lost in the transition. To fully achieve the objective of on-site, complete evaluation of margin sufficiency, whether by visual inspection or radiographic evaluation, there must be a manner of intuitively orienting the tissue sample such that if one or more of the margins contain cancerous cells, the surgeon will know which area of the patient requires additional tissue removal.

There have been several attempts in the prior art to evaluate a biopsy specimen via a particular type of container or device. However, as outlined below, the prior art has not provided for a container providing a non-compressed, orthogonal view of the tissue sample, which would fully allow the viewer or radiographic instrument to evaluate whether every margin of the removed sample is free from cancerous cells, while at the same time providing a quick and intuitive method of orienting the sample inside the container, which would allow for on-site evaluation of the tissue sample, thereby allowing a surgeon to remove the appropriate amount of tissue from the patient without requiring additional surgery following an off-site evaluation of the sample.

U.S. Pat. No. 5,383,472, issued on Jan. 24, 1995 to Mark T. Devlin et al. for "Method and Apparatus for Handling of Biopsy Tissue Specimen," discloses a self-contained set of imaging apparatus which permit an excised tissue to be handled, inked, and imaged in radiology and transported to pathology untouched by human hands. Absolute margins of tissue are inked by solution, and injected into sealed, disposable bag from syringe attached to the bag. Inked tissue is removed from bag and placed upon fluid-absorbent Hotter inscribed with radiographically opaque grid, inside of transparent container. Hinged top and bottom panels of liquid-tight container secure tissue in place. Tissue is visible from outside of container during transport, X-ray imaging, and subsequent pathologic evaluation. Further, the image presented to the pathologist with the inked tissue permits extremely accurate identification of locations of suspect element. The pathologist can easily view the enclosed, undisturbed sample and associated radiograph prior to dissection, which can be done with said apparatus if so desired.

U.S. Application Publication No. 2005/0112758, published May 26, 2005 by Meaghan Archambault et al. for "Method and Apparatus for the Storage of a Tissue Specimen," discloses a device that is provided for transporting a tissue specimen without the risk of exposing health-care workers to potentially hazardous tissue fluids. The device includes a container, a flexible portion, a first support member, a first locating indicia on a first side of the first supporting member, and a second substantially radiopaque locating indicia on a second side of the first support member, and an indicating member movably mounted on the first side of the first support member. The first support member has a first locating indicia on a first surface and a second locating indicia on a second surface, which generates a radiographic image when exposed to X-rays. The first and second indicia are substantially in registration such that when a tissue specimen is positioned on the first locating indicia and is then exposed to X-rays, a radiographic image of the specimen superimposed on the image of the second locating indicia is produced. Since both locating indicia are in registration, any tissue abnormality within the specimen can be precisely located with respect to both indicia. The device further includes a second support member, limiting contact of the container walls with the tissue specimen, and biasing the flexible portion away from the first support surface containing the tissue specimen. The device further includes an at least partially radiopaque indicating member for indicating the position of the tissue specimen on the radiographic image. A method for using the device to generate radiographic images of a tissue specimen is also disclosed.

U.S. Pat. No. 5,609,827, issued on Mar. 11, 1997 to Donald G. Russel et al. for "Biopsy Specimen Container," discloses a container that has a bottom surface and an outer wall extending from the bottom surface. A sheet of absorbent material lines the bottom surface. A container cover engages with the outer wall. The cover, wall, and bottom define an internal chamber. A divider is mounted within the chamber to form a central compartment and a plurality of peripheral compartments. Radiographically, readable indicia identify each compartment.

U.S. Pat. No. 6,238,907, issued on May 29, 2001 to Doris Schuler-Maloney et al. for "Container for Storing and Examining Placentas," discloses a container for examination and storage of a placenta that includes a bottom wall, at least one substantially upright side wall joined to the bottom wall to define an interior and an open top. The side walls and/or the bottom wall have indicia thereon adapted to measure the size of the placenta in three dimensions. Indicia are also provided to measure the umbilical cord. The container is stackable for storage, and labeling areas are provided. A basic method of examining a placenta is disclosed, along with further steps and variations.

U.S. Pat. No. 4,131,998, issued on Jan. 29, 1979 to Cohn P. Spears for "Tumor Growth Measurement Device," discloses a device for measuring growth of tumors, and includes concentric rings on a carrier, the radial spacing of the rings from one another progressively increasing in a radially outward direction. The invention relates generally to the measurement of tumor growth, and more particularly to a simple indicator which may be placed over a tumor to measure growth rate.

It may be appreciated from the foregoing that there is a need in the art for a method and apparatus that provides for appropriate evaluation of a removed tissue sample, for determination of whether the margins are sufficiently clear of cancerous cells.

It is therefore an object of the present invention to provide for an apparatus that displays a 360-degree view of a tissue specimen to the observer.

It is a further object of the present invention that said 360-degree view is provided with 90-degree indicators, such that the observer may evaluate the location of cancerous cells in an intuitive, orthogonal orientation.

It is a further object of the present invention to provide an apparatus that may hold the tissue specimen in a non-compressed manner so that the specimen is undistorted during evaluation.

It is a further object of the present invention to provide an apparatus that is simple to enact and easy to transport, allowing for the quick and intuitive on-site observation of the removed tissue sample, and further ensuring the integrity of the orientation of the sample when it is transported for radiographic evaluation, which in turn may give a surgeon the opportunity to remove additional tissue as needed prior to completion of the initial surgery.

SUMMARY OF THE INVENTION

The present invention achieves the above objectives by providing apparatus primarily composed of three elements: an end cap, a top cap, and a flexible, transparent piece of material. The tissue, upon removal from the patient, will feature a physical stitch in the tissue sample oriented at one of the six orthogonal positions of the patient's body. The handler of the tissue sample will place the sample on the piece of flexible, transparent material, and orient the stitch of the tissue sample with a notch provided on the flexible, transparent material. The flexible, transparent material also features a slit or series of slits in its side, so that the handler may then gently roll the flexible material around the tissue sample and lock it into a spherical configuration via the slit or slits on the side of the material. Given the variety of sizes of material and slit positions available in the present invention, the handler would be able to roll the sheet of material around the tissue sample in such a manner that the tissue sample will be suspended within the material, but not compressed or unduly distorted. After the sample is encased in the transparent material, the rolled material is inserted into the end cap of the apparatus. This end cap features a series of lined, circular grooves, meant to receive the rolled material. The end cap, crucially, also features an indicator conveying the appropriate location of the stitch from the tissue sample. When the tissue sample, encased in the rolled material, is placed in this appropriate position of the end cap, the integrity of the relative positions and angles of the tissue sample are ensured. The top cap is then placed on the opposite end of the tissue sample, securing the placement of the flexible, transparent material. By capping both ends, the handler may easily transport the sample to the appropriate evaluator, such as the pathologist, for analysis. In such transport, the relative position of the cancerous cells within the tissue sample will always remain certain, given the orientation of the stitch in the sample. Because the sample is encased in a transparent tube, each orthogonal angle of the sample, and its corresponding margins, may be evaluated, and such information may then be conveyed to the surgeon while on-site and available to most appropriately conclude or continue the surgical procedure.

BRIEF DESCRIPTION OF DRAWINGS

Reference will now be made to the drawings, wherein like parts are designated by like numerals, and wherein:

FIG. 1 is an overview of the present invention in use;

FIG. 2 is an apparatus representative of the prior art;

FIG. 9 is an exploded view of the present invention in use, according to one embodiment of the present invention;

FIG. 10 is a schematic view of the present invention in use, according to one embodiment of the present invention; and FIG. 11 is a view of the present invention of use, depicting the apparatus at a first angle and at a 180-degree rotation from said first angle.

DETAILED DESCRIPTION OF THE INVENTION

Figure 3:
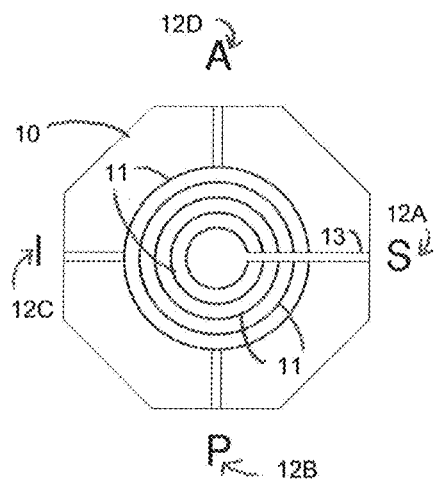
FIG. 3 is a schematic view of the bottom cap of the apparatus according to one embodiment of the present invention.

Referring to FIG. 1 generally, the present invention provides for an apparatus 100 featuring an end cap 10, a flexible plastic sheet 20, and top cap 30. The end cap 10 features a series of lined grooves embedded in the end cap. The flexible plastic sheet 20, when rolled into a round or spherical configuration, may be fitted into one of lined grooves embedded in the end cap 10. After being placed in the appropriate circular groove, the top cap 30, which also features a series of lined grooves embedded into one side of the top cap 30, is placed on the top end of the rolled plastic sheet 20 and the plastic sheet 20 fit into the appropriate lined groove of the top cap 30. Upon placement of the top cap 30 and end cap 10 on the rolled plastic sheet 20, the tissue specimen 40, which may include cancerous cells 50, contained within the sheet 20 will remain suspended and ready for examination by the handler of the apparatus 10.

FIG. 2 is an example of the conventional manner of encapsulating a tissue specimen 40 for examination. The tissue specimen 40 is encased within a transparent container, which allows for the observer, such as the pathologist, to determine whether the margins of the tissue sample 40 are free from cancerous cells. However, it may be appreciated that the conventional apparatus, as depicted in FIG. 2, provides no point of reference for the observer. Instead, it merely suspends the tissue specimen 40 in the container for visual inspection, without orienting the specimen to the handler. Further, the suspension is effected at 120-degree angles, which are non-intuitive to a surgeon or pathologist trained to evaluate a tissue sample 40 at the conventional 90-degree set of angles.

Figure 4:
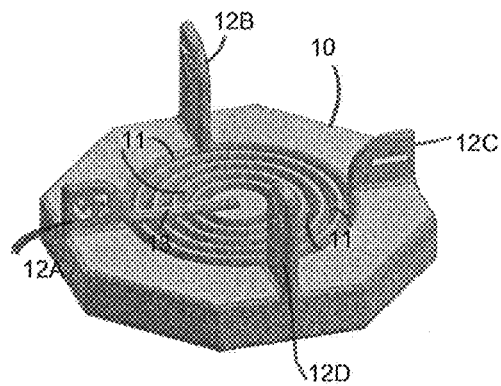
FIG. 4 is a perspective view of the bottom cap of the apparatus according to one embodiment of the present invention.

Referring back to the present invention, FIGS. 3 and 4 depict a preferred embodiment of the end cap 10 of the tissue specimen device 100. The end cap 10 includes grooves 11 lined into the surface of the end cap 10. The grooves 11 are of such width to accept placement of the plastic sheet 20 whereby placing the plastic sheet 20 into the groove 11 will allow easy placement and removal, but where the sheet 20 will not fall out of said groove 11 without the holder purposefully removing the sheet 20 from the selected groove 11.

In the preferred embodiment of the bottom cap, these grooves 11 may be featured as a series of concentric grooves 11 embedded in the surface of the end cap 10, as depicted in FIGS. 3-4. The varied diameter of each concentric groove 11, relative to the other concentric grooves 11, in turn allows for a varied diameter of the plastic sheet 20 to be placed into the groove 11. Depending on the size of the tissue sample 40 that will be placed on the plastic sheet 20, the plastic sheet 20, when rolled, may have a diameter as short as, for example, one centimeter, or as long as, for example, four centimeters. The relative diameter of the plastic sheet 20, when rolled, is dependent on the size of the tissue sample 40 placed on the plastic sheet. It may be appreciated that when rolling the plastic sheet 20 around the tissue specimen 40 placed on the sheet 20, it is desirable to create a spherical encasement that suitably holds the sample 40 in place but does not compress the sample 40 by rolling the sheet 20 too tightly around the sample 40. Thus, allowing for flexibility of the ultimate diameter of the plastic sheet 20, when rolled around the tissue specimen 40, ensures that the tissue sample 40 will not be compressed and thus distorted during examination of the sample 40.

As shown schematically in FIG. 3 and in perspective in FIG. 4, the bottom cap may feature indicators 12A-D, positioned around the edge of the bottom cap. The indicators 12A-D are placed at relative positions 0°/360°, 90°, 180°, and 270° around the circumference of the end cap 10. As depicted in FIG. 4, the indicators 12A-D, in a preferred embodiment, may be a type of "flag" arising out of the bottom of the bottom of the end cap 10 to display to the holder the relative locations of the four indicators 12A-D.

The indicators may be preferably labeled with the letters "A," "P," "S," and "I," referring to the relative "anterior," "posterior," "superior," and "inferior" positions of the end cap, as shown schematically in FIG. 3 and in perspective in FIG. 4. It may be appreciated by those in the art that "anterior" and "posterior" refer to relative "front" and "back" ends of a tissue; that is, the "anterior" side of such a sample refers to the side of the sample closer to the outside of the body, while the "posterior" side of such a sample refers to the side of the sample closer to the inside of the body. Similarly, "superior" and "inferior" refer to the "above" and "below" ends of a tissue sample, such as the side of the tissue sample located closer to the head of the person operated upon (the "superior" end) versus the side of the tissue sample located closer to the feet of the person operated upon (the "inferior" end). It may be appreciated that those skilled in surgery regularly refer to tissue samples by these indicators, and use same when evaluating any abnormalities that may be located within the tissue sample collected from the person operated upon.

The end cap also features a notch 13, preferably featured at the "superior" position of the end cap 10. The superior notch 13 acts as a stitch receptor for when the rolled plastic sheet 20 is placed in the appropriate concentric groove 11 of the end cap 10. The standard method of orienting a tissue sample 40 is performed via orientation of a stitch present in every removed tissue sample 40, located at the superior end of the sample 40. By placing the notch/stitch receptor 13 at the appropriate location of the end cap 10, the sample 40 encased in the plastic sheet 20 will always be properly oriented for quick, intuitive analysis of the sample 40 by the pathologist.

It may be appreciated that the placement and labeling of the indicators 12A-D may be varied in different embodiments of the present invention. The depiction in FIGS. 3 and 4 is merely a preferred embodiment, but the present invention may also function with simply the notch 13, as placement of the superior stitch in the notch 13 of the end cap 10 is sufficient to identify the proper orientation of the sample 40. The indicators 12-D and labels discussed herein and depicted in FIGS. 3 and 4 merely emphasize the orientation of the sample and provide additional, intuitive indications of the orientation of the sample 40 to the observer so as to aid in quick mental orientation of the tissue sample 40 when analyzing potential abnormalities in the sample 40.

Similarly, the present invention is not meant to be limited to any specific number of concentric grooves 11 in the end cap 10, but may feature any number of concentric grooves 11. For example, the apparatus may be provided with a series of differently-sized end caps 10, each featuring similar or different numbers and sizes of concentric grooves 11. One such end cap 10 may feature, for example and without limitation, a single circular groove 11 with a diameter of 1.5 cm. Another end cap 10 may feature, for example and without limitation, four concentric grooves 11 with diameters ranging between 0.5 cm-5.0 cm. The number and diameter of the concentric grooves 11 are meant to be flexible within the apparatus 100, given the varied size of tissue samples 40 that may be expected to be removed from a patient.

Figure 5:
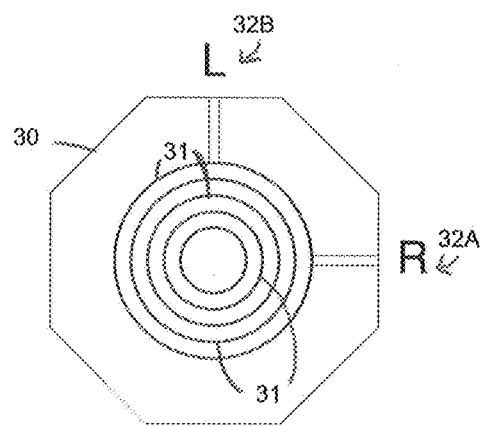
FIG. 5 is a schematic view of the top cap of the apparatus according to one embodiment of the present invention.

FIG. 5 depicts a preferred embodiment of the top cap 30 of the apparatus 100 of the present invention. The top cap 30 features, like the end cap 10, a circular groove 31 or set of concentric grooves 31 lined into the surface of the top cap 30. Said circular grooves 31 of the top cap 30 are meant to mirror the circular grooves 11 featured in the end cap 10. In this manner, when the rolled plastic sheet 20 is placed in the appropriate circular groove 11 of the end cap 10, the top cap 30 may fit appropriately over the opposite end of the rolled plastic sheet 20. Like the grooves 11 of the end cap 10, the grooves 31 of the top cap 30 are not meant to be limited to any number of grooves 31 or certain diameter of groove 31. The top cap 30, like the end cap 20, may instead feature a variety of grooves 31 in a single top cap 30 or set of top caps 30.

As shown in FIG. 5, top cap 30 may optionally feature an indicator 32 or indicators 32A-B of the type that may be featured on the end cap 10. Such top cap 30 indicators 32A-B may, for example, be labeled with indicia "L" or "R," referring to the left or right side of the cap 30, further providing an orientation guideline for the handler. However, such indicia are not necessary, as the notch/stitch receptor 13 provided in the end cap 10 provides the relative orientation of the tissue sample 40 as necessary for accurate analysis of the sample 40.

Figure 6:
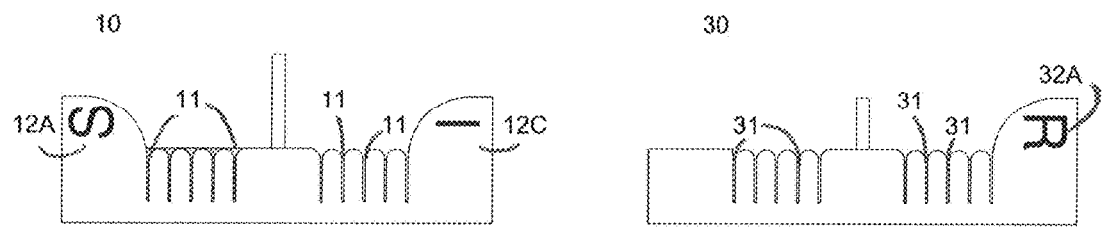
FIG. 6 is a schematic view of the bottom and top caps of the apparatus according to one embodiment of the present invention, taken in profile.

FIG. 6 depicts the profile view of the end cap 10 and top cap 30, respectively. As shown in the two caps 10 and 30 of FIG. 6, the grooves 11 and 31 featured in the end and top caps 10 and 30 of the apparatus 100 are concentric, meaning that they provide a circular, symmetrical receptacle for the ends of the plastic sheet 20 when rolled and placed in the end cap 10 and capped on top with the top cap 30. The grooves 11 and 31 may be provided of a depth sufficient to ensure the plastic sheet 20 is secure in the cap 10 or 30; for example, the groove 11 or 31 may extend approximately three-quarters of the depth of the end cap 10 and top cap 30.

Figure 7:
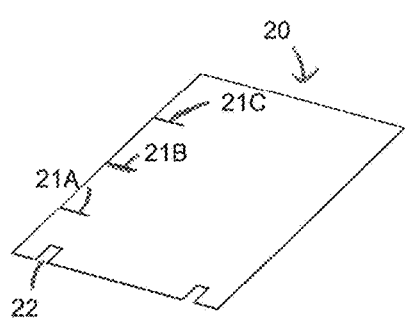
FIG. 7 is a schematic view of the plastic sheet of the present invention.
Figure 8:
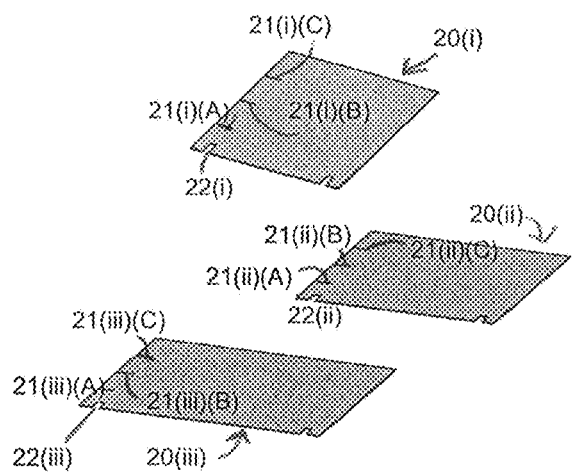
FIG. 8 is a view of the multiple plastic sheets of the present invention.

Referring now to FIGS. 7 and 8, said figures depict examples of the plastic sheets 20(*i*)-(*iii*) of the present invention. Plastic sheets 20(*i*)-(*iii*) may be composed of any transparent, flexible material, provided that the material is able to be rolled in a spherical configuration around a removed specimen, and provides the appropriate visual opportunities to a visual inspection or the radiographic equipment employed for radiographic evaluation of the sample.

FIG. 7 illustrates how the plastic sheet 20 may include a slit 21 or slits 21A-C along one side of the plastic sheet 20. The slit 21 is provided in the plastic sheet 20 so that the plastic sheet 20 may be secured in place when rolled around the tissue sample 40 to be evaluated by the apparatus 100. For example, in use, the user of the present invention will place the tissue sample 40 on the plastic sheet 20. The user will then roll the plastic sheet 20 around the tissue sample 40 so that the plastic sheet 20 encases the tissue sample 40 appropriately. The end of the plastic sheet 20 is then placed in the appropriate slit 21 to secure the plastic sheet 20 in its rolled, spherical position around the sample 40.

In rolling the plastic sheet 20 around the tissue sample 40, as noted above, the user would take care to roll the sheet 20 tightly enough to ensure the tissue sample 40 will be secured, but not so tightly as to compress and distort the sample 40. The provision of slit 21 or slits 21A-C in the plastic sheet 20 allow this varied diameter of the plastic sheet 20, so that it may be of appropriate diameter to hold the tissue sample 40 in place without distorting the sample 40. For example, placement of the end of the plastic sheet 20 around slit 21C will provide a "tighter" roll around the sample 40 than, for example, placement into slit 21A.

As shown in FIG. 8, the plastic sheets 20(*i*)-(*iii*) may be of varied size, and with varied placement of the slit 21 or slits 21A-C in the side of the plastic sheet 20, so as to provide for maximum options when appropriately rolling the tissue sample 40. It may be noted that while FIGS. 7 and 8 depict a plastic sheet 20 with multiple slits 21A-C, the spirit and object of the present invention may be achieved with a single slit 21 in the side of the plastic sheet 20, provided there are alternate plastic sheets 20(*i*)-(*iii*) available. For example, a user may wish to use the apparatus 100 with several plastic sheets 20(*i*)-(*iii*), each with only one notch 21 in its side but of varied size. By varying the size of the plastic sheet 20, the user will obtain the same options in rolling the tissue sample 40 into the appropriate diameter. For example, instead of choosing between slits 21A and 21C when choosing the appropriate diameter for encasing the tissue sample 40, the user would choose between plastic sheet 20(*i*) and 20(*iii*), which would similarly offer varied potential diameters for encasing the tissue sample 40.

As noted in FIGS. 7 and 8, plastic sheet 20 also features sheet notches 22. These sheet notches 22 provide for the reception of the stitch of the tissue sample 40, which is present in the tissue sample 40 when removed from the body. As discussed above, the presence of such a stitch is a matter of custom in the surgical arts. In addition to providing a manner of securing the tissue sample 40 on the plastic sheet 20, by attaching the stitch to the appropriate notch 22, the placement of the stitch in the notch 22 also provides a manner of orienting the tissue sample 40 to the pathologist observing the sample. As discussed above, the location of the stitch is customarily located in the superior position of the tissue sample 40. Thus, by securing the stitch in the notch 22 of the plastic sheet 20, the observer will know how to properly orient the rolled plastic sheet 20 in the end cap 10 and mentally orient the tissue sample 40, providing for proper evaluation of the margins of properly-oriented tissue sample 40. It may be appreciated that this frame of reference also allows for the correct information to be conveyed back to the surgeon, who is awaiting instruction by the pathologist of whether to remove additional tissue from the patient, and if so, from which section of the sample site.

Turning now to FIG. 9, the apparatus 100 is shown in an exploded perspective view. FIG. 9 depicts the end cap 10, ready for reception of the plastic sheet 20; the plastic sheet 20 as rolled around a tissue sample; and the top cap 30, ready to secure the apparatus 100. As shown in FIG. 9, the plastic sheet 20, when rolled around a tissue sample, will be of such a diameter as to fit into one of the concentric grooves 11 of the end cap 10. The user slides the rolled plastic sheet 20 into the appropriate groove 11, lining up the sheet notch of the plastic sheet 20 with the stitch notch 13 of the end cap 10.

FIG. 10 depicts the preferred embodiment of the apparatus 100 when it is ready to be evaluated by the specimen handler. As depicted in FIG. 10, the plastic sheet 20 fits into the appropriate groove 11 of the end cap 10, and the top cap 30 similarly fits on top of the opposite end of the rolled plastic sheet 20. The plastic sheet 20, encasing the tissue sample, is thus secured between the two caps 10 and 30 of the apparatus 100 and ready for evaluation. The configuration of the apparatus also ensures that the sample will remain secured and fixed in the appropriate position when transported to the pathologist for the on-site analysis of the sample and throughout the handling of the sample.

FIG. 11 depicts the apparatus 100A-B of the present invention in use, shown from two separate angles 100A and 100B, taken at 90-degree angles to each other. Tissue sample 40 is encased within the plastic sheet 20, secured within the apparatus 100A-B by the application of the end cap 10 and top cap 30. As shown in FIG. 11, there may be cancerous cells 50 within the tissue sample 40. It may be appreciated that use of a transparent plastic sheet 20 to encase the tissue sample 40 allows the observer to view these cancerous cells 50 and, more importantly, their orientation within the tissue sample 40. For example, View 100A of the S-I side of the sample 40 in FIG. 11 shows that the cancerous cells 50 are located approximately midway between the superior and inferior position of the overall tissue sample. It may be appreciated by those in the surgical art that View 100A depicts a favorable tissue sample, because the tissue surrounding the cancerous cells (the "margins" 60) are free of cancerous cells 50. The "margins" 60 of the tissue sample, as they are referred to by those in the art, are meant to be clear of such cancerous cells 50. An observer of the sample as shown in View 100A of FIG. 11 would thus conclude that the tissue 40 removal was sufficient, because it is likely that the cancerous cells 50 were removed from the patient. However, View 100B, taken at a 90-degree angle from the View 100A of the S-I side of the sample 40, shows the sample 40 as oriented to its relative anterior and posterior positions. As shown by way of example in FIG. 11, the cancerous cells 50 are close to the edge of the anterior position of the sample (that is, are "within the margin" 60). As may be appreciated by those in the art, such an orientation of the cancerous cells 50 indicates that the anterior margin 60 of the tissue sample is not sufficiently clear of such cancerous cells 50. A pathologist evaluating the tissue sample 40 of FIG. 11, when analyzing View 100B of the A-P side of the sample, would conclude that additional tissue must be removed from the patient to ensure that the anterior border of the cancerous site is sufficiently clear of cancerous cells. The pathologist may then convey this information to the surgeon, who may then remove the additional tissue, from the appropriate side of the surgical site, as required.

FIG. 11, as described above, illustrates the application of the instant invention. First, it displays to the viewer a full view of the tissue sample, rather than evaluating a compressed, two-dimensional sample as provided by some examples of the prior art. When only evaluating four margins (i.e., top, bottom, left, and right), the tissue sample may deceptively appear to be free of cancerous cells. However, as illustrated by View 100B of FIG. 11, there may be cancerous cells in the fifth or sixth margin of the tissue sample. This is the reason those skilled in the art employ such orthogonal evaluation of tissue samples, rather than relying on a flat representation of the sample. Second, when evaluating all six angles of the sample, it is crucial that the observer be able to quickly and properly orient the margins as related to the patient in surgery. By way of example, in View 100B of FIG. 11, the evaluator of the apparatus would quickly and intuitively know that the anterior margin of the sample is not sufficiently clear of cancerous cells. The surgeon would thus remove an appropriate extra amount of tissue from the anterior area of the surgical site on the patient to ensure that all cancerous cells were removed.

It may be appreciated that the provision of the intuitive orientation of the margins allows for on-site evaluation of the tissue sample. In the prior art, margin evaluations had to be conducted after the conclusion of surgery. Many times, after a patient was released from surgery, a thorough evaluation of the removed tissue sample would reveal that the margins were not clear in the removed sample. The patient would thus have to undergo a second surgical procedure to remove additional tissue from the area with unclear margins. In using the present invention, a surgeon would be able to perform the second extraction of tissue during the original surgical procedure, thereby eliminating the need for the patient to undergo additional surgery.

Many changes and modifications can be made in the present invention without departing from the spirit thereof. I therefore pray that my rights to the present invention be limited only by the scope of the appended claims.

I claim:

1. An apparatus for the evaluation of a surgically removed tissue sample, comprising:
    (i) a sheet of clear material adapted to be rolled into a cylinder to enclose said surgically removed tissue sample after removal; and
    (ii) an end cap and a top cap adapted to accommodate said sheet of clear material when rolled into a cylinder, where said end cap or said top cap is provided with an indicator tab identifying a standard indicator of orientation of said surgically removed tissue sample;
    where said surgically removed tissue sample has an orientation relative to a patient's body prior to removal from said patient's body;
    where said surgically removed tissue sample is placed by the surgeon onto said sheet of clear material and encased between said top cap and said bottom cap in a proper orientation corresponding to said orientation of said surgically removed tissue relative to said patient's body prior to removal; and
    where an examiner's observation of the tissue sample after removal will be provided with all necessary information regarding said proper orientation of said surgically removed tissue sample.

2. The apparatus of claim 1, wherein said sheet of clear material includes at least one slit along an edge of said sheet of clear material, to allow for said sheet of clear material to be rolled into a cylinder of a certain diameter to enclose said surgically removed tissue sample after removal.

3. The apparatus of claim 2, further comprising:
(iii) a second sheet of clear material, wherein said second sheet of clear material includes at least one slit along an edge of said second sheet of clear material, to allow for said second sheet of clear material to be rolled into a cylinder of a certain diameter differing from said certain diameter of first said sheet of clear material.

4. The apparatus of claim 2, wherein said end cap comprises a cylindrical-shaped groove of a certain diameter embedded in the surface of said end cap, for reception of a bottom edge of said sheet of clear material; and wherein said top cap comprises a cylindrical-shaped groove embedded in the surface of said top cap of the same said certain diameter as said cylindrical-shaped groove embedded in the surface of said end cap, for reception of a top edge of said sheet of clear material.

5. The apparatus of claim 4, further comprising:
(iii) a second end cap and a second top cap, wherein said second end cap comprises a cylindrical-shaped groove of a second diameter embedded in the surface of said end cap, for reception of a bottom edge of said sheet of clear material, and wherein said second top cap comprises a cylindrical-shaped groove embedded in the surface of said top cap of the same said second diameter as said cylindrical-shaped groove embedded in the surface of said second end cap, for reception of a top edge of said sheet of clear material.

6. The apparatus of claim 2, wherein said end cap comprises at least two cylindrical-shaped grooves of varying diameters embedded in the surface of said end cap, for reception of a bottom edge of said sheet of clear material when rolled into a cylinder around said surgically removed tissue sample; and wherein said top cap comprises at least two cylindrical-shaped grooves of varying diameters embedded in the surface of said top cap, wherein said at least two cylindrical-shaped grooves of said top cap are of the same diameter as said at least two cylindrical-shaped grooves of said end cap, for reception of a top edge of said sheet of clear material.

7. The apparatus of claim 1, wherein said sheet of clear material includes multiple slits along an edge of said sheet of material, to allow for said sheet of clear material to be rolled into a cylinder of varying diameters.

8. The apparatus of claim 1, wherein said end cap or said top cap is provided with a notch receptor for alignment with a stitch present in said surgically removed tissue sample.

9. The apparatus of claim 1, wherein said end cap is octagonal, featuring eight edges, with four of said eight edges at ninety-degree angles to each other, and wherein said indicator tab is located along one of said eight edges, such that said examiner of the tissue sample may properly orient each of said four sides of said tissue sample.

10. A method of evaluating a surgically removed tissue sample, comprising:
(i) removing a tissue sample from a patient;
(ii) placing said tissue sample on a sheet of clear material, said sheet of clear material adapted to be rolled into a cylinder to enclose said tissue sample after removal;
(iii) rolling said sheet of clear material into a cylinder to enclose said tissue sample;
(iv) placing a bottom edge of said cylinder into an end cap; and
(v) placing a top cap over a top edge of said cylinder;
where said end cap and said top cap are adapted to accommodate said sheet of clear material when rolled into a cylinder;
where said end cap and said top cap are provided with an indicator tab identifying a standard indicator of orientation of said tissue sample;
where said tissue sample has an orientation relative to said patient's body prior to removal; and
where an examiner's observation of said tissue sample after removal will be provided with all necessary information regarding said proper orientation of said tissue sample.

11. The method of claim 10, wherein said sheet of clear material includes at least one slit along an edge of said sheet of clear material to allow for said sheet of clear material to be rolled into a cylinder of a certain diameter to enclosed said tissue sample after removal.

12. A method of evaluating a surgically removed tissue sample, comprising:
(i) removing a tissue sample from a patient;
(ii) using an apparatus to evaluate said tissue sample, said apparatus comprising:
(a) a sheet of clear material adapted to be rolled into a cylinder to enclose said tissue sample after removal; and
(b) an end cap and a top cap adapted to accommodate said sheet of clear material when rolled into a cylinder, where said end cap or said top cap is provided with an indicator tab identifying standard indicators of orientation of said tissue sample;
where said surgically removed tissue sample has an orientation relative to said patient's body prior to removal from said patient's body;
(iii) placing said tissue sample onto said sheet of clear material; and
(iv) encasing said sheet of clear material between said end cap and said top cap in a proper orientation corresponding to said orientation of said tissue sample relative to said patient's body prior to removal;
where an examiner's observation of said tissue sample after removal will be provided with all necessary information regarding said proper orientation of said tissue sample.

13. The method of claim 12, wherein said sheet of clear material includes at least one slit along an edge of said sheet of clear material, to allow for said sheet of clear material to be rolled into a cylinder of a certain diameter to enclosed said tissue sample after removal.

14. The method of claim 13, wherein said apparatus further comprises:
(c) a second sheet of clear material, wherein said second sheet of clear material includes at least one slit along an edge of said second sheet of clear material, to allow for said second sheet of clear material to be rolled into a cylinder of a certain diameter differing from said certain diameter of first said sheet of clear material.

15. The method of claim 13, wherein said end cap comprises a cylindrical-shaped groove of a certain diameter embedded in the surface of said end cap, for reception of a bottom edge of said sheet of clear material; and wherein said top cap comprises a cylindrical-shaped groove embedded in the surface of said top cap of the same said certain diameter of said cylindrical-shaped groove embedded in the surface of said end cap, for reception of a top edge of said sheet of clear material.

16. The method of claim 15, wherein said apparatus further comprises:
(c) a second end cap and a second top cap, wherein said second end cap comprises a cylindrical-shaped groove of a second diameter embedded in the surface of said end cap, for reception of a bottom edge of said sheet of clear material, and wherein said second top cap comprises a cylindrical-shaped groove embedded in the surface of said top cap of the same said second diameter as said cylindrical-shaped groove embedded in the surface of said second end cap, for reception of a top edge of said sheet of clear material.

17. The method of claim 13, wherein said end cap comprises at least two cylindrical-shaped grooves of varying diameters embedded in the surface of said end cap, for reception of a bottom edge of said sheet of clear material when rolled into a cylinder around said tissue sample; and wherein said top cap comprises at least two cylindrical-shaped grooves of varying diameters embedded in the surface of said top cap, wherein said at least two cylindrical-shaped grooves of said top cap are of the same diameter as said at least two cylindrical-shaped grooves of said end cap, for reception of a top edge of said sheet of clear material.

18. The method of claim 12, wherein said sheet of clear material includes multiple slits along an edge of said sheet of material, to allow for said sheet of clear material to be rolled into a cylinder of varying diameters.

19. The method of claim 12, wherein said end cap or said top cap is provided with a notch receptor for alignment with a stitch present in said tissue sample after removal.

20. The method of claim 12, wherein said end cap is octagonal, featuring eight edges, with four of said eight edges at ninety-degree angles to each other, and wherein said indicator tab is located along one of said eight edges, such that said examiner of said tissue sample may properly orient each of said four sides of said tissue sample.

\* \* \* \* \*